United States Patent [19]
Hackenberg

[11] Patent Number: 5,237,878
[45] Date of Patent: Aug. 24, 1993

[54] APPARATUS AND METHOD FOR SAMPLING ULTRA-PURE CHEMICAL

[75] Inventor: Diana L. Hackenberg, Palm Bay, Fla.

[73] Assignee: Sematech, Inc., Austin, Tex.

[21] Appl. No.: 982,107

[22] Filed: Nov. 24, 1992

Related U.S. Application Data

[63] Continuation of Ser. No. 724,692, Jul. 2, 1991, abandoned.

[51] Int. Cl.$^5$ .............................................. G01N 1/14
[52] U.S. Cl. .............................. 73/864.34; 73/863.33; 73/863.83
[58] Field of Search ........... 73/864.73, 863.81–863.85, 73/864.34, 864.35, 863.33,

[56] References Cited

U.S. PATENT DOCUMENTS

| | | | |
|---|---|---|---|
| 2,906,126 | 9/1959 | Brown | 73/863.83 |
| 3,864,978 | 2/1975 | Stephens | 73/422 GC |
| 3,901,653 | 8/1975 | Jones et al. | 23/230 R |
| 3,922,920 | 12/1975 | Chandler | 73/422 |
| 3,994,170 | 11/1976 | Czarnecki | 73/863.51 |
| 3,999,945 | 12/1976 | Kushner et al. | 23/253 |
| 4,002,066 | 1/1977 | Ratigan | 73/170 A |
| 4,037,475 | 7/1977 | Topham | 73/422 R |
| 4,052,904 | 10/1977 | Kushner et al. | 73/421 R |
| 4,077,263 | 3/1978 | Brailsford | 73/421 B |
| 4,078,433 | 3/1978 | McCabe et al. | 73/425.4 |
| 4,109,837 | 8/1978 | Taylor | 222/556 |
| 4,157,664 | 6/1979 | Robinson | 73/425.4 |
| 4,213,342 | 7/1980 | Gates | 73/421 B |
| 4,302,974 | 12/1981 | Niskin | 73/864.6 |
| 4,305,279 | 12/1981 | Ontek | 73/155 |
| 4,317,378 | 3/1982 | Mustard | 73/863.1 |
| 4,347,751 | 9/1982 | Niskin | 73/864.33 |
| 4,593,570 | 6/1986 | Niskin | 73/864.67 |
| 4,594,903 | 6/1986 | Johnson | 73/863.83 |
| 4,612,815 | 9/1986 | Green et al. | 73/864.11 |
| 4,625,574 | 12/1986 | Robbins | 73/864.6 |
| 4,628,749 | 12/1986 | Rafter, Jr. | 73/863.71 |
| 4,736,637 | 4/1988 | Stock | 73/863.83 |
| 4,823,623 | 4/1989 | Carpenter et al. | 73/864 |
| 4,852,413 | 8/1989 | Niskin | 73/864 |
| 4,857,473 | 8/1989 | Magaritz et al. | 436/177 |
| 4,930,360 | 6/1990 | Tan | 73/864.34 |
| 4,941,360 | 7/1990 | McClellan et al. | 73/863.83 |
| 4,999,307 | 3/1991 | Oakley | 436/180 |
| 5,029,485 | 7/1991 | Marr | 73/864.34 |

FOREIGN PATENT DOCUMENTS 2632727 12/1989 France ........................... 73/864.34

Primary Examiner—Robert Raevis
Attorney, Agent, or Firm—William W. Kidd

[57] ABSTRACT

An ultra-pure chemical sampling apparatus has an elongated sampling tube which is lowered into the liquid to obtain samples of the chemical. The sampling tube extends the depth of the liquid and holes arranged along the tube provides for a representative sample to be obtained at different depths. The sampling tube is coupled to a collection bottle by a tubing of which a section of flexible tubing is coupled to a peristaltic pump to pump the liquid up the sampling tube, through the tubing and into the collection bottle. A cap is used to seal the sampling tube and a secondary containment receptacle is used to enclose the bottle in order to inhibit the escape of chemical fumes which could harm the environment or the person obtaining the sample.

9 Claims, 2 Drawing Sheets

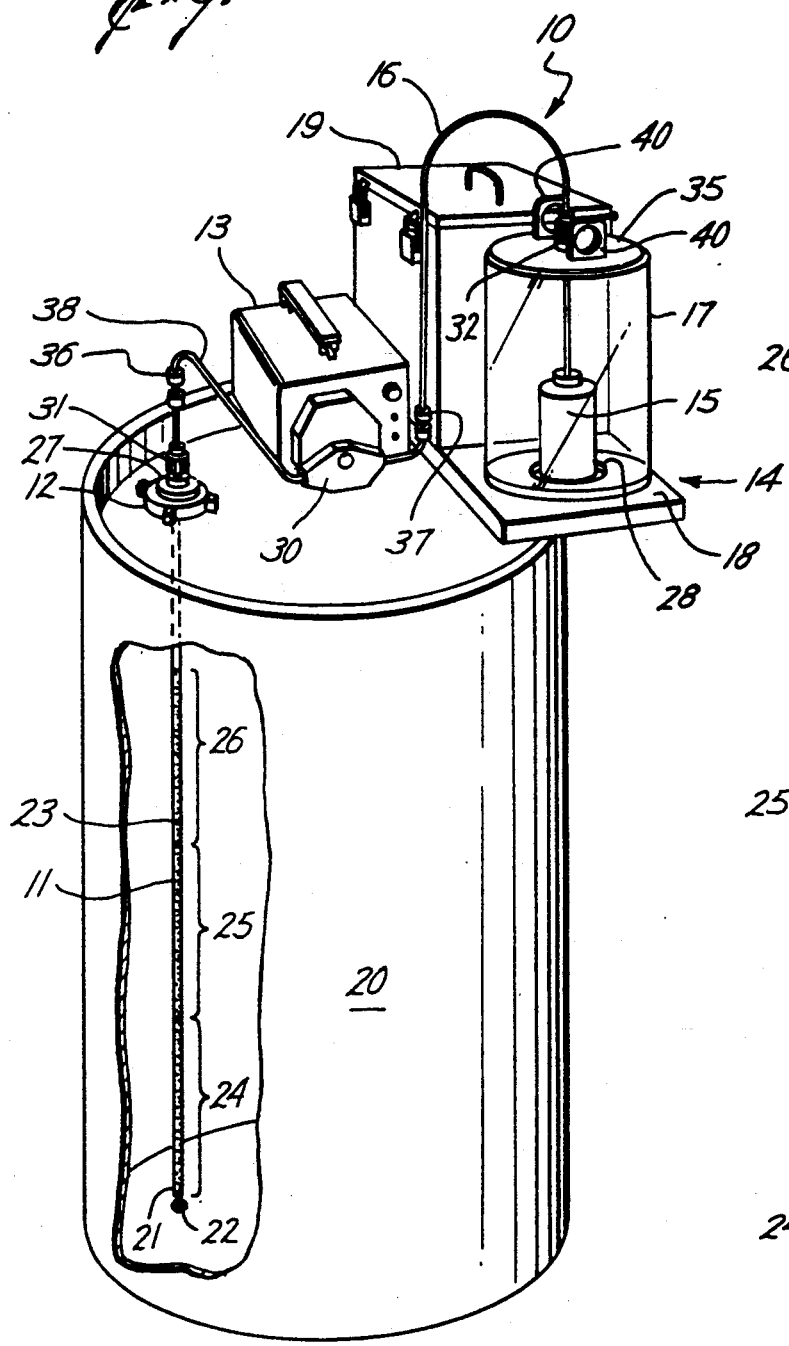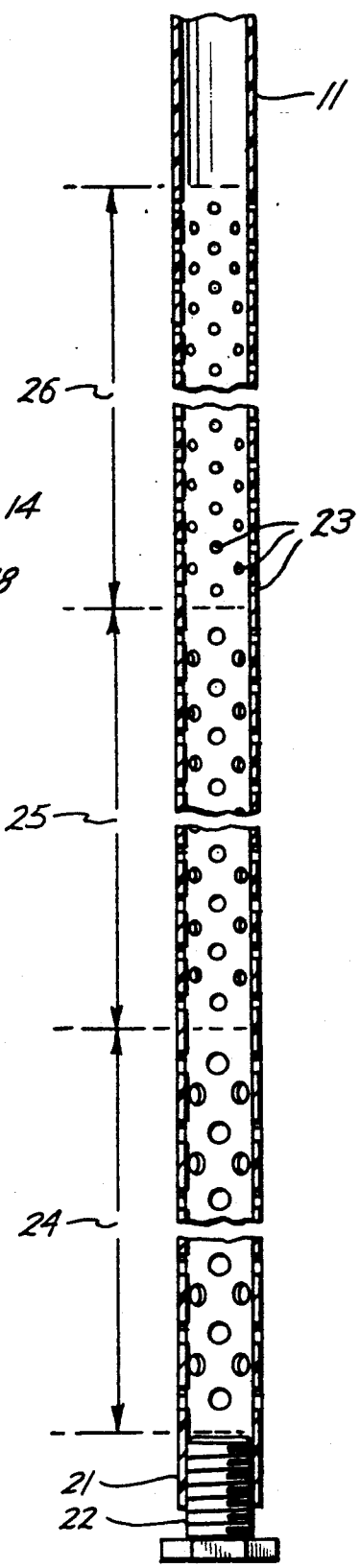

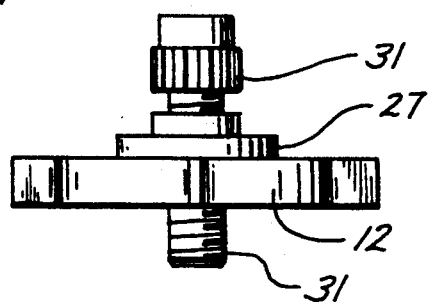
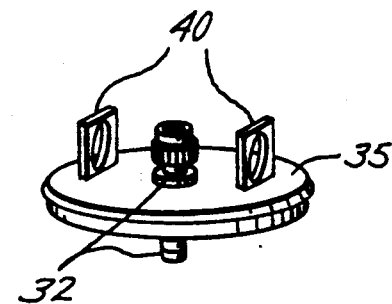
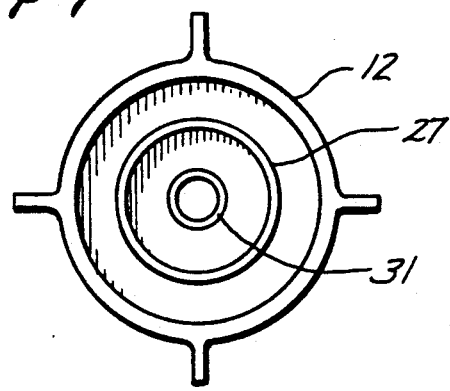
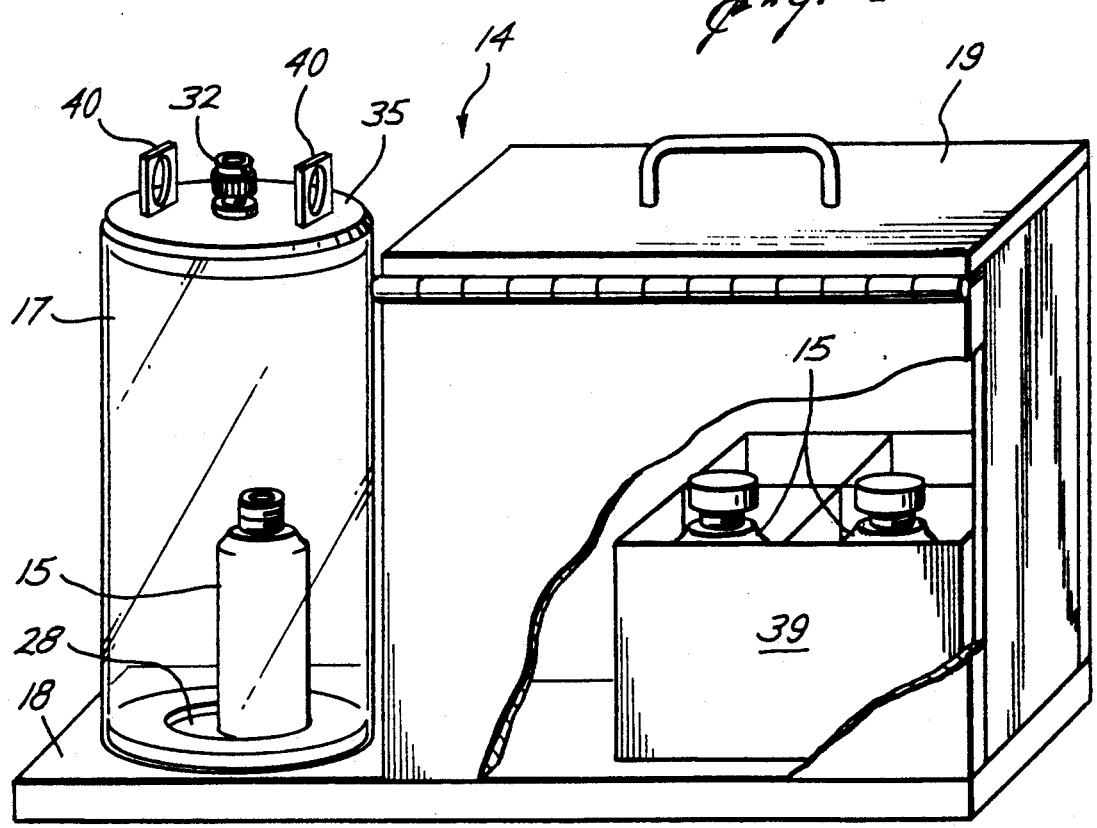

APPARATUS AND METHOD FOR SAMPLING ULTRA-PURE CHEMICAL

This application is a continuation of application Ser. No. 724,692, filed Jul. 2, 1991, now abandoned.

BACKGROUND OF THE INVENTION

1. Field of the Invention

The present invention relates to the field of fluid sampling devices and, more particularly, to a device and method for sampling ultra-pure chemicals.

2. Prior Art

Various devices and techniques are well-known in the prior art for sampling fluids, especially liquids. The most primitive of these techniques is the lowering of an open sampling container into the liquid and withdrawing the container once it is filled with a sample of the liquid. A refinement to this simple sampling container is an apparatus which encloses and confines the sampling liquid once the sample is taken. Typically, these type of containers are lowered into the liquid and once the container holds the sample, the container is "capped" in order to retain the liquid. This technique also prevents the sample from being contaminated as the container is withdrawn from the liquid. A device utilizing this technique is described in U.S. Pat. Nos. 4,305,279 and 4,852,413.

In most instances, a significant number of these devices are utilized for sampling water. When sampling water, it is not critical to preserve the sample in an ultra clean environment. The intent of maintaining sample integrity is typically of concern when the water sample is being withdrawn through a confined area which could introduce contaminants into the sample.

However, when liquids other than water are concerned, maintaining purity of the sample may be a critical concern as the sample is removed from the liquid source. It is imperative to maintain the purity of the sample to reflect the actual condition of the liquid being sampled. It is also imperative that the liquid source is not contaminated during the sampling procedure. Once such apparatus and method for withdrawal of liquid samples from a sterile liquid source is described in U.S. Pat. No. 4,999,307. Furthermore, various other closed systems are well-known in the prior art for taking samples from a liquid source in a confined system. For example, U.S. Pat. No. 3,922,920 describes a technique for providing the capture of a fluid sample from a fluid source, utilizing a chamber whose metering portion holds a pre-set volume of fluid. U.S. Pat. No. 4,213,342 describes a sampling device which samples by the use of a connected source of pressure to cause movement of sampled liquid in and out of a sealed container.

Although the art is populated by devices and techniques for taking samples from a liquid source, the field is narrowed considerably when samples are to be taken from ultra-pure chemicals which may be hazardous to the human operator. Further limitation is encountered when such sampling devices are to be made portable.

For example, in the processing of semiconductor wafers, ultra-pure chemicals are necessary to process semiconductor wafers to fabricate integrated circuit (IC) devices. The semiconductor industry dictates the use of the purest chemicals made. The chemicals used include concentrated acids and bases, which can degrade many of the commercially available sampling devices. Typically these chemicals are required to have less than 10 parts per billion (ppb) of most metals. However, due to the ever improving technology of IC fabrication, metal contaminants will need to be reduced to 1 ppb or less. This requirement will dictate that any method employed to obtain a representative sample be able to do so without contaminating the chemical. Thus, samplers made from metals, borosilicate glass and polyethylene cannot be used.

The ultra-pure chemicals are typically received in "drums" from a supplier of the chemical and the contents are typically tested prior to usage, such as during "receiving inspection". In this instance, a human operator will take samples from each of drums and remove those samples to a central testing facility, such as a chemical laboratory, and determine the purity of the chemical under inspection. Therefore, a number of stringent constraints are placed on the device and technique utilized for taking such samples.

The sampling apparatus must be portable and must not present undue burden to the operator in transporting and manipulating the apparatus. Furthermore, the apparatus must be capable of taking representative samples from the drum while maintaining a substantially clean environment in order not to contaminate the liquid source or the sample being taken. The collected sample must be maintained in an environment which is not susceptible to contamination while being transported back to the laboratory. Finally, the sampling apparatus and technique must not cause the operator to be subjected to the toxic or hazardous chemicals and fumes during the sample taking procedure.

Two of the better chemical sampling devices known in the prior art are described below. A chemical sampling kit utilizing a syringe type head for drawing samples from acid sinks and large canisters into a clean container is one of the simpler portable devices used in the testing of chemicals. One such chemical sampling kit is sold by Balazs Analytical Laboratory of Sunnyvale, California. In another apparatus, a peristaltic pump is utilized. Instead of the use of a syringe type head, a peristaltic pump is used to pump the liquid from the drum in order to draw the sample. Other simpler tools are also being used currently to draw liquid chemical samples from the drum. Such tools are commonly referred to as coliwasas, bailers, and grab samplers. Typically, the use of these devices requires that the drum containing the chemical be left opened to the environment during the sampling process, which exposure is more than sufficient to contaminate the drum.

Although these various prior art devices may function adequately in taking samples from chemical containers, they present a number of disadvantages (or short comings) to the semiconductor industry as requirements for chemicals having low levels of contaminants are needed. The present invention provides an apparatus and technique in order to meet the needs of taking samples of ultra-pure chemicals, particularly when these chemicals are for use in IC fabrication.

SUMMARY OF THE INVENTION

An ultra-pure chemical sampling apparatus and method are described. An elongated non-metallic sampling tube is inserted substantially the full depth of the liquid. The upper end of the sampling tube is coupled through a bulkhead fitting of a modified container cap ("head"). The lower end of the sampling tube is terminated by a nylon screw. The sampling tube is perforated with holes wherein the diameter of the holes are dependent on the locations of the holes in relation to the depth sampling tubes. Larger diameter holes are used deeper in the liquid to obtain homogenous samples from various depths of the liquid.

One end of a separate tubing is coupled to the external side of the sampling tube, while the other end is coupled to a collection bottle. This tubing has a flexible section which is coupled to a peristaltic pump for siphoning the liquid out of the container through the holes located on the sampling tube.

The collection bottle is placed in a covered, transparent receptacle in order to contain harmful fumes and provide secondary containment during the sampling period. A box with the receptacle is provided to transport pieces of the apparatus while keeping them free of contamination. Inside the receptacle a raised ring provides a stable platform for the bottle while the sample is being collected. Because of the containment of the liquid and the fumes, a person obtaining the sample is not exposed to a hazardous environment if the fumes are toxic. The containment of the liquid and the fumes of the drum also ensure that the chemical is not contaminated from external sources.

BRIEF DESCRIPTION OF THE DRAWINGS

FIG. 1 is an illustration of an apparatus of the present invention positioned on a chemical containing drum.

FIG. 2 is an elongated sampling tube of the present invention.

FIG. 3a is a view of a modified drum return head of the present invention.

FIG. 3b is a bottom plan view of the modified drum return head of FIG. 3a.

FIG. 4 is a pictorial view of the box which is used to transport the various tubings, fittings and collection bottles which are used to obtain the sample and also shows the receptacle attached to the extended base of the box.

FIG. 5 is a pictorial view of the cover of the receptacle.

DETAILED DESCRIPTION OF THE PREFERRED EMBODIMENTS

The present invention describes an apparatus and method for taking representative samples from an ultra-pure liquid source. In the following description numerous specific details are set forth, such as specific structure, shape, material, etc., in order to provide a thorough understanding of the present invention. It will be obvious, however, to one skilled in the art that the present invention may be practiced without these specific details. In other instances well-known methods and structures have not been set forth in order not to unnecessarily obscure the present invention.

The semiconductor industry dictates the use of the purest chemicals for fabrication of semiconductor integrated circuits (ICs). These various chemicals, which include concentrated acids and bases, must maintain purity levels of less than 10 parts per billion (ppb) of most metal contaminants. However, as processing technology is enhanced to provide for submicron-dimensioned devices, especially for ICs being fabricated utilizing 0.5 micron (or less) technology, the metal contaminant levels will need to be reduced to 1 ppb or less. The apparatus of the present invention provides for the taking of homogeneous (representative) samples from a ultra-pure chemical source without contaminating the sample, the source, the surrounding environment, and providing for a non-harmful condition for the person obtaining the sample.

Referring to FIG. 1, a sampling apparatus 10 of the present invention is shown. Apparatus 10 is comprised of an elongated sampling tube 11, tubing 16, a pump 13, and a housing 14, which includes a collection bottle 15 and receptacle 17 for collecting the liquid sample. Apparatus 10 also includes a cap 12 (commonly referred to as a "head"), specially adapted for use with a particular container holding the ultra-pure chemical.

In the particular example of FIG. 1, the ultra-pure chemical is resident within a container typically known as a drum 20, which drum is used to transport the chemical from the supplier to the user. The drum 20 has one or more openings available for accessing the liquid. Because these drums 20 are typically stored upright, the opening(s) is/are located at the upper cylindrical end of the drum 20. It is common practice for these chemical containing drums 20 to have a pair of circular openings. One opening is utilized for distribution of the chemical, while the second opening is utilized as a return for the purpose of equalizing the internal pressure of the drum as the chemical is withdrawn from the drum through the distribution opening. A threaded fitting is placed in the openings. A cap, (or head) is tightly fitted onto each of these fittings in order to seal the chemical within. A cap for use on the return opening is referred to as a "return head".

As can also be noted in FIG. 2, the elongated sampling tube 11 is hollow and terminated at the distal end 21. In the preferred embodiment, the distal end 21 is threaded on the inside of the tube and terminated by the use of a nylon screw 22. The sampling tube 11 is perforated by a plurality of randomly placed holes for the purpose of siphoning the liquid into the interior of tube 11. The diameter of the holes 23 vary according to the location of the hole in relation to distal end 21. The holes toward the distal end 21 are of a selected diameter and the diameter of the holes 23 gradually decrease as they are located farther from distal end 21.

The sampling tube 11 of the preferred embodiment utilizes three different hole sizes. A lower section 24 closest to distal end 21 contains holes 23 having a diameter of 0.052 inches. A center section 25 of the elongated tube 11 includes holes 23 having a diameter of 0.044 inches, while the upper section 26 closest to the head 12 includes holes 23 having a diameter of 0.040 inches. The purpose of the varying size holes relative to the position on the elongated tube 11 is to provide for a homogenous sampling of the liquid in drum 20 as will be described later.

The other end of the sampling tube 11 is coupled to head 12. As can also be seen in FIGS. 3a and 3b, head 12 is a specially constructed cap which is adapted to fit onto one of the drum openings. In the preferred embodiment the cap 12 is utilized with the return opening of drum 20, although in practice it can be modified to operate with most any opening. Head 12 is modified from a standard design of a cap normally used to seal drum 20. Head 12 is adapted to have central disk 27, which is actually an insert made form polypropylene or other non-contaminating polymeric material. A hole is drilled completely through disk 27 and a fitting 31 is placed into this hole. Although a variety of fittings can be used, the preferred embodiment uses a screw-type bulkhead fitting 31. Bulkhead fittings are utilized for passage of items, such as tubing, through the wall (bulkhead) and can have tighteners to fasten the item securely in the fitting.

The open end of sampling tube 11 is coupled through fitting 31 and thus through head 12. After the placement of tube 11 through fitting 31, head 12 can be disposed to fit onto the return opening of drum 20, providing for the sampling tube 11 to extend into the liquid of drum 20, so that holes 23 are well below the level of the liquid. The free end of sampling tube 23 is coupled to a coupling 36.

One end of a coupling tubing 16 is coupled to fitting 36 while the other end of the tubing 16 is placed through bulkhead fitting 32, into receptacle 17 and into the opening of bottle 15. Disposed between head 12 and receptacle 17, and coupled to tubing 16 is the pump 13. Pump 13 is used to provide a peristaltic force on tubing 16 for siphoning the liquid up through sampling tube 11, through tubing 16 and into bottle 15.

Also referring to FIGS. 4 and 5, housing 14 of the preferred embodiment is shown comprised of a sample collection bottle 15, a receptacle 17, a cover 35, a box 19 and a flat base extension 18 of box 19. The box 19 is rectangular in shape having a hinged upper lid which permits access to the interior of the box when opened. A section of the box includes a divided compartment 39 for storing a number of bottles 15. The box also includes a handle for carrying the housing 14. The bottom base of the box extends further than the box to provide an extended base 18.

The receptacle 17 is cylindrical in shape having a base with a circular cutout 28 at the bottom. The base end of the receptacle is permanently bonded to the extended base 18. The bottle 15 is positioned within cutout 28 and cutout 28 aids in preventing the bottle from toppling over during sample collection. A cover 35 is placed over the upper opening of receptacle 17. Tubing 16 extends through the fitting 32 of cover 35 and into the opening of bottle of 15. The purpose of receptacle 17 is to retain any vapors which may escape from the opening of bottle 15, as well as providing secondary containment if there is spillage from the bottle 15.

Cover 35 fits tightly onto the upper opening of receptacle 17. In actual practice, the inner surface of the cover 35 is notched to fit the inner diameter of the upper end of receptacle 17. Handles 40 are affixed to the outer surface of cover 35 for its removal from receptacle 17. The box 19 is used to transport the tubings, fittings, bottles, etc., needed for obtaining samples, while keeping these items from being contaminated during transport. It is also used to transport bottles containing samples once a sample has been obtained. In instances where the sampling tubes are difficult to retain in the box 19, they can be transported separately in a "clean" bag.

The pump 13 of the preferred embodiment is a peristaltic pump for pumping the liquid from drum 20. A variety of peristaltic pumps, or their equivalents, are available commercially and one such peristaltic pump is manufactured by Cole-Palmer Instrument Company of Chicago, Ill.

It is appreciated that any of the material coming in contact with the liquid must be free of contaminants and further must not introduce contaminants into the liquid. Although a variety of plastic material and/or polymeric material can be readily adapted for use as the material of choice, the preferred embodiment utilizes a fluoro-containing polymeric material commonly trademarked as TEFLON TM (TEFLON is a registered trademark of E.I. Dupont de Nemours and Company). The tubes and all fittings are constructed from TEFLON material. Although the disk 27 of head 12 can be made of the TEFLON material, it is actually made from polypropylene, since it is rare for disk 27 to come in contact with the liquid. Polycarbonate material is also used for receptacle 17, cover 35 and box 19 since these items also should not come in contact with the liquid.

Because TEFLON tubes tend to have a hardened surface, a peristaltic pump, such as the one utilized with the present invention, may not have the capability of peristaltically pumping the liquid with TEFLON tubes. In order to overcome this problem, tubing 16 of the preferred embodiment, has an added section of flexible tubing 38. Instead of having tubing 16 coupled to coupling 36 for feed through of the liquid, tubing 16 is coupled to a feed through coupling 37. Flexible tubing 38 is coupled between couplings 36 and 37. Couplings 36 and 37, which are made from TEFLON material, are utilized to provide a section of flexible tubing 38, such that the pumping head 30 of the peristaltic pump 13 is coupled to flexible tubing 38. Although a variety of flexible tubing can be utilized for this purpose, the preferred embodiment utilizes a flexible polycarbonate tubing trademarked as TYGON TM (TYGON is a trademark of Morton Company of Worcester, Mass.). The TYGON tubing is flexible so that the pumphead 30 can apply the peristaltic action for obtaining the sample.

It is to be noted that fluoro-containing material, such as TEFLON material be used for those items which the fluid comes into contact, since fluoro-containing materials are generally the least contaminating. When flexibility is needed (such as for peristaltic action) or when the contaminant level need not be in the lower ppb, polycarbonate material can be used. Polycarbonate materials tend to produce more contaminants then fluoro-containing materials. Glass is undesirable since it contains silicon.

The operation of the apparatus 10 of the present invention is as follows. The open end of sampling tube 11 is inserted through the bulkhead fitting 31 in the head 12. In a standard 55 gallon drum the holes 23 need to be at least eight inches below the drum return opening. Tubing 38 is coupled to coupling 36 for feed through while the other end of tubing 38 is coupled to coupling 37 for feed through fitting 32 and inserted into the bottle 15. The TYGON tube section 38 is coupled into the head 30 of the peristaltic pump 13. The bottle 15 is placed in the cutout 28 of receptacle 17. Cover 35 is placed tightly onto receptacle 17. The receptacle 14 and the pump 13 are of sufficiently small size that these devices can be positioned atop drum 20. It is to be appreciated that if tubing 16 is sufficiently flexible for peristaltic operation, tubing 38 is not needed and tubing 16 can be directly coupled to fitting 36.

Then, the original drum cap is removed from the drum and the sampling tube 11 is inserted through the opening, typically the return opening (also commonly referred to as the return "bung"). The modified head 12 is then screwed into place and tightened.

The external end of each of the bulkhead fittings 31 and 32 will typically have a tightening sleeve which is screwed down to prevent the movement of the sampling tube 31 and/or tubing 16. Each coupling 36 and 37 will have a pair of such sleeves to clamp the tubes coupled to it.

The pump 13 is activated to pump the liquid through holes 23, up the sampling tube 11 through tubing 38 and tubing 16 and collected in bottle 15. The speed of the sample collection can be controlled by controlling the speed of the pump 13. When the collection is completed, pump 13 is turned off. The tube section 38 can be removed from the pumphead 30 such that some of the liquid remaining in tubing 16 can be made to return to drum 20 or further collect in bottle 15. The cover 35 is lifted to cap bottle 15 and remove it from receptacle 17. The bottle 15 is then stored in box 19 for transport.

Cover 35 is replaced quickly after bottle 15 removal. The head 12 is then unscrewed and sampling tube 11 removed from drum 20. The original drum head is replaced quickly to seal the drum 20. Also during this process, any of the fittings can be readily loosened to disconnect any or all portions of the sampling tube 11 and tubing 16, if desired. For example, fitting 31 can be loosened and sampling tube 11 pulled up prior to head 12 removal. Since most of the tube 11 is out of the drum 20, tube 11 removal can be achieved much more quickly. In some instances, the tubings of couplings and fittings of the apparatus 10, as well as bottle 15 and sampling tube 11, can be flushed by taking one or more samples. The bottle 15 can be emptied when filled during this flushing process to remove any initial contaminants present in the sampling flow route. The pumphead should not be disconnected during this procedure in order to prevent any liquid from returning into the drum 20 and contaminating it.

The advantages of the present invention are many fold over the prior art. For example, it is common practice to roll the drum to mix the liquid prior to taking a sample when utilizing a prior art sampling apparatus. However, in the present invention, samples are taken at various depths of the liquid. Due to the plurality of holes 23 which extend approximately the length of the drum 20, a homogeneous sample is capable of being taken without the need for mixing the contents prior to such sample taking. Further, the varying size holes along the length of tube 11, ensure that equal volume of liquids is being pulled at the varying sampling levels. That is, the holes near the pump as shown by section 26 will have more suction than the more distant holes of section 24. In order to alleviate this difference in the siphoning rate, tube 11 ensures that the same amount of fluid enters the tube 11 at all sections 24, 25, and 26. It is to be appreciated that an alternative approach is to have same diameter holes at all levels but that to increase the number of holes per unit length as distance increases down the sampling tube 11 from head 12.

Another advantage results when head 12 is utilized to reseal the opening during sample removal. Thus, if the sampling process takes more than a nominal amount of time to collect the sample, fumes are not introduced into the atmosphere during the sampling process due to the exposed drum opening. Any amount of time that the liquid is exposed to the ambient, even nominal, will result in some chemical to be released as fumes, which fumes can be hazardous. More importantly, the rapid reseal ensures that the operator is not harmed in the event the fumes from the chemical are hazardous or toxic.

Once the sample has been collected, the bottle 15 is capped and placed in box 19 for transport. The tubings 11, 16, 38 as well as the fittings and couplings can be collected, or alternatively discarded. It is to be noted that because receptacle 17 is transparent, the operator can determine when to stop the pump 13 by observing the level of the liquid in bottle 15.

Because the physical dimensions of the apparatus 10 of the present invention is sufficiently small in size, the apparatus can easily fit atop the standard drum. Also, because of its relatively light weight, a person can easily transport the apparatus and necessary tools to the location of the chemical, obtain the sample and transport the items, including the sample liquid to its destination. The sampling tube 11 and cap 12 can be easily adapted to function with various size drums and bungs.

The preferred embodiment uses a sampling tube 11 which has three different size holes 23 wherein each holes section 24, 25 and 26 is approximately 12 inches long. A quarter inch tubing is used throughout for tubings 11, 16 and 38. The box 19 is 8×13 inches and is 11 inches high. The compartment 39 holds four bottles and is 8×7½ inches, with a height of 5 inches. The base 18 extends another 8 inches to provide a total length of 21 inches with the inclusion of the box 19. The receptacle 17 is 11 inches high and is made from a 6½ inch PVC. The sides of receptacle 17 is made from clear PVC piping. The cutout 29 is 3 inches in diameter. The cover 35 is also cut from PVC. The box 19 and base 18 are made from polypropylene.

Furthermore, it is appreciated that the present invention can be used to sample the drum other than at "receiving inspection". For example, when drums are coupled to a chemical distribution system, which distributes the chemical to various equipment in a semiconductor fab, the apparatus of the present invention can be used to analyze the liquid in the drum during operation. The sampling tube is inserted in the return opening of the drum for obtaining samples.

Thus, an ultra-pure chemical sampling device and technique are described.

I claim:

1. A hand-carried portable apparatus for obtaining a sample from an enclosed container having a liquid chemical utilized for semiconductor manufacturing contained therein comprising;

a cap adapted for fitting over an opening of said container in order to prevent leakage of fumes of said chemical from said container;

a collection container for collecting said sample of said liquid;

an elongated sampling tube having a plurality of holes disposed along its length wherein a distal section of said sampling tube has holes of relatively larger openings as compared to holes located at other portions of said sampling tube and wherein a proximal section adjacent to a proximal end of said sampling tube has holes of relatively smaller openings as compared to holes located at other portions of said sampling tube, such that when said sampling tube is inserted into said liquid and its proximal and coupled to and through said cap, a pumping action initiated at said proximal end provides for drawing of said liquid from various depths of said enclosed container and wherein said pumping action causes relatively more suction to draw said liquid at said proximal end than at said distal end, but is compensated by smaller openings at said proximal end in order to obtain a representative sample quantity of said liquid from various levels of said enclosed container;

a tubing having one end coupled to said proximal end of said sampling tube and its other end coupled to said collection container.

2. The apparatus of claim 1 wherein said sampling tube, tubing and collection container are constructed from a non-metallic, non-corrosive material.

3. The apparatus of claim 1 wherein said sampling tube, tubing and collection container are constructed from a fluoro-containing material.

4. The apparatus of claim 1 wherein said collection container includes a transparent secondary container for retaining fumes emanating from said collection container and spillage from said collection container while obtaining said sample.

5. A hand-carried, portable apparatus for obtaining a homogenous sample from an enclosed container having an ultra-pure chemical in liquid form and which is utilized for semiconductor manufacturing contained therein, while inhibiting the escape of chemical fumes into the ambient comprising;
a cap adapted for fitting over an opening of said container in order to prevent leakage of fumes of said chemical from said container while said sample is being obtained, said cap having a central opening for drawing said liquid out from said container;
a fitting disposed in said central opening of said cap;
a collection container for collecting said sample of said liquid;
an elongated sampling tube having a plurality of holes disposed along its length wherein holes disposed farther from the end coupled to said cap have relatively larger diameter openings as compared to holes located at other portions of said sampling tube and holes disposed proximal to said cap have relatively smaller diameter openings as compared to holes located at other portions of said sampling tube, such that when said sampling tube is inserted into said liquid and a peristaltic pumping action is initiated, causing more suction at said end coupled to said cap than at other portions of said sampling tube, said plurality of holes having different diameter openings at various depths compensate for drawing of said liquid from various depths of said container in order to obtain a homogenous sample quantity of said liquid from said container, said sampling tube coupled to said first fitting;
a non-metallic tubing having one end coupled to said sampling tube and its other end coupled to said collection container;
a peristaltic pump coupled to said tubing for providing peristaltic pumping action to draw said liquid into said sampling tube, through said tube and into said collection container.

6. The apparatus of claim 5 wherein said collection container includes a transparent secondary container for retaining fumes emanating from said collection container and spillage from said collection while obtaining said sample.

7. The apparatus of claim 6 wherein said sampling tube, tubing and collection container are constructed from a fluoro-containing material, and has a section of said tubing coupled to said peristaltic pump constructed from a polycarbonate material.

8. A method for obtaining a sample from an enclosed container having a liquid chemical utilized for semiconductor manufacturing contained therein while inhibiting the escape of chemical fumes into the ambient, comprising the steps of:
attaching an elongated sampling tube, having a plurality of holes disposed along its length, through a cap for sealing an opening of said container, wherein holes of said sampling tube disposed farther from the end coupled to said cap have relatively larger diameter openings as compared to holes located at other portions of said sampling tube and holes disposed proximal to said cap have relatively smaller diameter openings as compared to holes located at other portions of said sampling tube;
attaching one end of a tubing to said cap end of said sampling tube and its other end to a collection bottle;
inserting said sampling tube into said opening of said container and sealing said opening by tightening said cap;
coupling a flexible section of said tubing to a peristaltic pump for pumping said liquid into said sampling tube, through said tubing and into said collection bottle, wherein said pumping causes relatively more suction to draw said liquid though holes disposed proximal to said cap, but said plurality of holes having different diameter openings at various depths compensate for drawing of said liquid in order to obtain a representative sample quantity of said liquid to be drawn from various depths of said container;
pumping to obtain said representative sample quantity from said container.

9. The method of claim 8 further comprising the step of placing said collection bottle in a sealed secondary container prior to drawing said sample.

* * * * *

UNITED STATES PATENT AND TRADEMARK OFFICE
CERTIFICATE OF CORRECTION

PATENT NO. : 5,237,878
DATED : August 24, 1993
INVENTOR(S) : Diana L. Hackenberg It is certified that error appears in the above-identified patent and that said Letters Patent is hereby corrected as shown below:

Column 1, line 42, "Once" should be --One--.

Column 2, line 13, insert --the-- between "of" and "drums".

Column 4, line 62, "form" should be --from--.

Column 8, line 55, "and" after "proximal" should be --end--.

Column 10, line 6, insert --container-- after "collection".

Signed and Sealed this

Second Day of August, 1994

Attest:

BRUCE LEHMAN

Attesting Officer     Commissioner of Patents and Trademarks